United States Patent
Kim et al.

(10) Patent No.: US 10,166,000 B2
(45) Date of Patent: Jan. 1, 2019

(54) RADIOGRAPHIC APPARATUS

(71) Applicant: Samsung Electronics Co., Ltd., Gyeonggi-do (KR)

(72) Inventors: Sung Nam Kim, Gyeonggi-do (KR); Seung Woo Shin, Gyeonggi-do (KR); Hyun Sun Kim, Gyeonggi-do (KR)

(73) Assignee: Samsung Electronics Co., Ltd., Yeongtong-gu, Suwon-si, Gyeonggi-do (KR)

(*) Notice: Subject to any disclaimer, the term of this patent is extended or adjusted under 35 U.S.C. 154(b) by 351 days.

(21) Appl. No.: 14/816,269

(22) Filed: Aug. 3, 2015

(65) Prior Publication Data
US 2015/0335307 A1 Nov. 26, 2015

Related U.S. Application Data

(63) Continuation of application No. 13/370,595, filed on Feb. 10, 2012, now Pat. No. 9,095,310.

(30) Foreign Application Priority Data

Feb. 15, 2011 (KR) .................. 10-2011-0013243

(51) Int. Cl.
*A61B 6/00* (2006.01)

(52) U.S. Cl.
CPC .............. *A61B 6/56* (2013.01); *A61B 6/4464* (2013.01); *A61B 6/467* (2013.01); *A61B 6/548* (2013.01)

(58) Field of Classification Search
CPC ....... A61B 6/4464; A61B 6/467; A61B 6/548; A61B 6/56
See application file for complete search history.

(56) References Cited

U.S. PATENT DOCUMENTS

| | | | |
|---|---|---|---|
| 6,027,247 A | * | 2/2000 | Tachi .................. A61B 6/0457 378/177 |
| 6,285,742 B1 | | 9/2001 | Haumann et al. |
| 2003/0091156 A1 | | 5/2003 | Crain et al. |

(Continued)

FOREIGN PATENT DOCUMENTS

| DE | 30 36 217 A1 | 4/1982 |
|---|---|---|
| EP | 0 506 172 A2 | 9/1992 |

(Continued)

OTHER PUBLICATIONS

European Search Report dated Nov. 26, 2016.
(Continued)

*Primary Examiner* — Glen Kao
(74) *Attorney, Agent, or Firm* — Cha+Reiter, LLC (57) ABSTRACT

Disclosed is a radiographic apparatus including a detachable manipulation panel which includes a capturing device to generate X-rays and to irradiate the X-rays to a subject so as to capture the subject, a controller connected to the capturing device to control the capturing device, and a manipulation device mounted to the capturing device to allow an inspector to input commands to control the capturing device, wherein the manipulation device is detachably mounted to the capturing device and, in a state in which the manipulation device is separated from the capturing device, is connected to the controller using a wireless interface to control the capturing device.

22 Claims, 7 Drawing Sheets

(56) References Cited

U.S. PATENT DOCUMENTS

| | | |
|---|---|---|
| 2006/0083353 A1* | 4/2006 | Boomgaarden ...... A61B 6/4464 378/196 |
| 2007/0189462 A1 | 8/2007 | Spahn |
| 2008/0069304 A1 | 3/2008 | Muszak et al. |
| 2008/0292056 A1 | 11/2008 | Marar |
| 2010/0152578 A1 | 6/2010 | Hall et al. |
| 2010/0189219 A1 | 7/2010 | Bowers et al. |
| 2010/0290598 A1 | 11/2010 | Marino |
| 2011/0306882 A1 | 12/2011 | Hannon et al. |
| 2012/0241567 A1 | 9/2012 | Gillespie-Brown et al. |

FOREIGN PATENT DOCUMENTS

| | | |
|---|---|---|
| JP | 2000-166907 A | 6/2000 |
| JP | 2003-210445 A | 7/2003 |
| JP | 2005-21470 A | 1/2005 |
| JP | 2007-000535 A | 1/2007 |
| JP | 2008-61765 A | 3/2008 |
| JP | 2008-173257 A | 7/2008 |
| KR | 10-2007-0036894 A | 4/2007 |
| KR | 10-0966883 B1 | 6/2010 |
| WO | 2011/132363 A1 | 10/2011 |

OTHER PUBLICATIONS

Korean Search Report dated Dec. 8, 2016.
Korean Search Report dated Oct. 22, 2016.
Chinese Notice of Allowance dated Sep. 6, 2016.
Korean Search Report, dated Mar. 3, 2016.
Korean Search Report dated Apr. 18, 2017.
Korean Decision on Grant dated Aug. 1, 2017 for KR Application No. 10-2017-0003118.

\* cited by examiner

RADIOGRAPHIC APPARATUS

CROSS REFERENCE TO RELATED APPLICATIONS

This application is a Continuation of U.S. patent application Ser. No. 13/370,595 filed on Feb. 10, 2012, now U.S. Pat. No. 9,095,310 issued Aug. 4, 2015, and which claims the benefit of the earlier filing date, under 35 U.S.C. § 119(a), of Korean Patent Application No. 10-2011-0013243, filed on Feb. 15, 2011 in the Korean Intellectual Property Office, the entire disclosure of which is incorporated herein by reference.

BACKGROUND

1. Field of the Invention

The present invention relates to a radiographic apparatus including a detachable manipulation panel.

2. Description of the Related Art

A radiographic apparatus is an apparatus that acquires images of the inner parts of a human body using X-rays. The radiographic apparatus is used to inspect bodily injuries or diseases in the inner parts of the human body which are not viewable from the exterior. The radiographic apparatus radiates X-rays towards the head or chest of the human body and then detects the X-rays transmitted through the head or chest of the human body to acquire images of the inner parts of the human body.

The radiographic apparatus includes an X-ray tube to radiate X-rays toward a region to be captured, a high voltage generator to generate high voltage to generate X-rays, and a shifter to shift the position and/or direction of the X-ray radiation. Also, the radiographic apparatus includes a manipulation device to allow an inspector (i.e., the operator of the radiographic apparatus) to perform manipulation to control the above devices.

Generally, the manipulation device includes a display unit to display a state of the radiographic apparatus and an input unit to allow an inspector to input commands. The manipulation device is provided in the form of a panel.

The manipulation device is fixedly mounted to one of the components which constitute the radiographic apparatus. Consequently, it may be necessary for an inspector to access the component of the radiographic apparatus to which the manipulation device is mounted. The component of the radiographic apparatus to which the manipulation device is mounted may be shifted to change the position and/or direction of the X-ray radiation with the result that the manipulation device may be beyond the inspector's reach or may be located where manipulation of the manipulation device by the inspector is difficult.

SUMMARY

Accordingly, an aspect of the present invention to provide a radiographic apparatus including a detachable manipulation panel.

Additional aspects of the invention will be set forth in the description which follows and variations thereof will be obvious to those of ordinary skill in the art after reading this description.

In accordance with an aspect of the present invention, a radiographic imaging apparatus includes a capturing device to generate X-rays and to radiate the X-rays towards a subject so as to capture an image of the subject, a controller connected to the capturing device to control the capturing device, and a manipulation device mounted to the capturing device to allow an inspector to input commands to control the capturing device, wherein the manipulation device is detachably mounted to the capturing device and, while in a state in which the manipulation device is separated from the capturing device, is connected to the controller using a wireless interface to control the capturing device.

The wireless interface may include any one selected from among infrared (IR) communication, radio frequency (RF) communication, Bluetooth communication, Wi-Fi communication and wireless USB communication.

The capturing device may include an X-ray irradiator to generate X-rays and to radiate the X-rays towards the subject, and the manipulation device may be detachably mounted to the X-ray irradiator.

The capturing device may include a high voltage generator to generate high voltage to generate the X-rays, and the manipulation device may manipulate a set value of the high voltage generator while in a state in which the manipulation device is separated from the capturing device.

The capturing device may include a high voltage generator to generate high voltage to generate the X-rays, and the manipulation device may manipulate the high voltage generator to generate high voltage while in a state in which the manipulation device is separated from the capturing device.

The capturing device may include a shifter to shift a radiation position at which the X-rays are generated and a direction in which the X-rays are radiated, and the manipulation device may manipulate the shifter while in a state in which the manipulation device is separated from the capturing device.

In accordance with another aspect of the present invention, a radiographic imaging apparatus includes a capturing device to generate X-rays and to radiate the X-rays towards a subject so as to capture an image of the subject, a controller connected to the capturing device to control the capturing device, a manipulation device connected to the controller to allow an inspector to input commands to control the capturing device and to display information on the capturing device, and a docking device provided at the capturing device so that the manipulation device may be detachably mounted to the capturing device through the docking device.

The manipulation device may include a wireless connection unit to transmit and receive a wireless signal.

The wireless connection unit may include any one selected from among an IR module, RF module, Bluetooth module, Wi-Fi module and wireless USB module.

The manipulation device may include a display unit to display information and an input unit to allow the inspector to input commands.

The input unit may include a touch panel configured to respond to touch of the inspector.

The input unit may include a shift manipulation unit to manipulate an irradiation position and direction of the X-rays.

The input unit may include a high voltage setting unit to set a value of high voltage to generate the X-rays.

The input unit may include a high voltage generation unit to perform manipulation to generate high voltage to generate the X-rays.

The input unit may include an inspector authentication unit to authenticate the inspector.

The manipulation device may include a battery unit to supply power to the manipulation device in a state in which the manipulation device is separated from the capturing device.

The docking device may include a power supply unit to supply power to the manipulation device while in a state in which the manipulation device is mounted to the docking device and a wired connection unit connected to the manipulation device using a wired interface.

The wired connection unit may include any one selected from among a serial communication module, USB module, IEEE1394 module and LAN module.

The power supply unit and the wired connection unit may be integrated.

The manipulation device may be rotatably mounted to the capturing device.

The docking device may include a rotary unit rotatably coupled to the capturing device and a mounting unit to which the manipulation device is mounted.

The mounting unit may include a mount hole formed in a shape corresponding to the manipulation device and a fixing protrusion to fix the manipulation device.

BRIEF DESCRIPTION OF THE DRAWINGS

The above and other aspects of the invention will become apparent and more readily appreciated from the following description of the embodiments, taken in conjunction with the accompanying drawings of which.

DETAILED DESCRIPTION

Reference will now be made in detail to the embodiments of the present invention, examples of which are illustrated in the accompanying drawings, wherein like reference numerals refer to like elements throughout. In the embodiments of the present invention, a manipulation device is applied to a ceiling type radiographic apparatus, in which a guide rail is mounted to the ceiling of an inspection room, although the manipulation device may be applied to various kinds of radiographic apparatuses.

Figure 1:
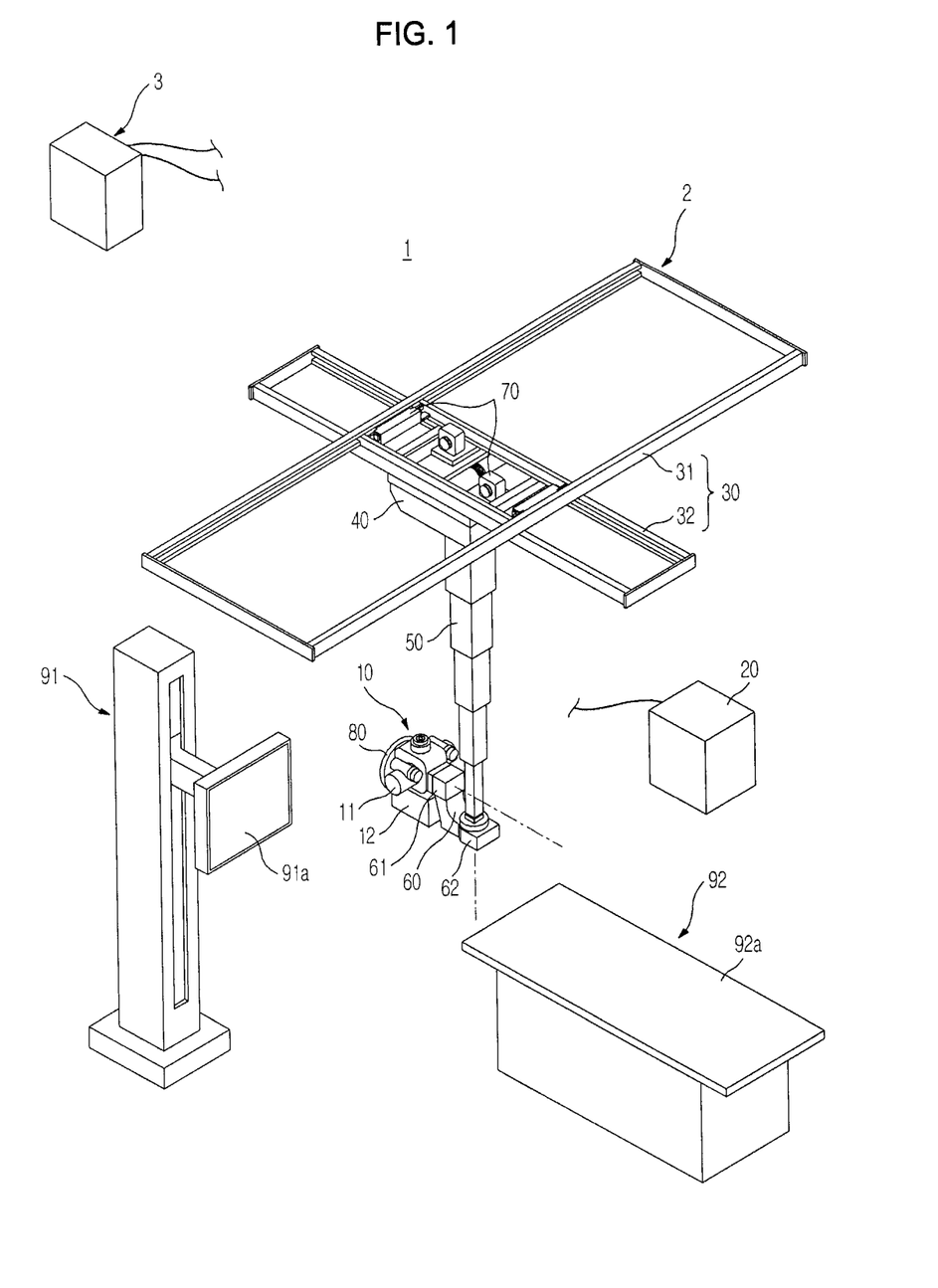
FIG. 1 is a view illustrating the main components of a radiographic apparatus according to an embodiment of the present invention.

FIG. 1 is a view illustrating the main components of a radiographic apparatus 1 according to an embodiment of the present invention.

As shown in FIG. 1, the radiographic apparatus 1 includes a capturing device 2 and a controller 3 to control the capturing device 2.

The capturing device 2 includes an X-ray irradiator 10 to radiate X-rays towards a subject, a high voltage generator 20 to supply high voltage to the X-ray irradiator 10 to cause it to generate X-rays, a capturing stand 91 and capturing table 92 having X-ray detectors 91a and 92a to receive X-rays transmitted through the subject, respectively, and a shifter to shift an X-ray irradiation position and direction of the X-ray irradiator 10.

The shifter includes a guide rail arrangement 30 mounted to the ceiling of an inspection room, a moving carriage 40 movable along the guide rail 30, a post frame 50 connected between the moving carriage 40 and the X-ray irradiator 10, and a drive device 70 to provide drive force to shift the guide rail 30, the moving carriage 40 and the post frame 50.

The guide rail 30 includes a first guide rail 31 and a second guide rail 32 forming a predetermined angle with the first guide rail 31. In the illustrated embodiment, the first guide rail 31 and the second guide rail 32 extend perpendicularly to each other.

An upper side of the first guide rail 31 is mounted to the ceiling of the inspection room in which the radiographic apparatus 1 is located. The second guide rail 32 is slidably mounted to the first guide rail 31 at the lower side of the first guide rail 31. At the first guide rail 31 may be disposed a roller mechanism (not shown) movable along the first guide rail 31. The second guide rail 32 may be connected to the roller mechanism (not shown) so that the second guide rail 32 is movable along the first guide rail 31.

The moving carriage 40 is disposed at the lower side of the second guide rail 32 so that the moving carriage 40 is movable along the second guide rail 32. At the moving carriage 40 may be disposed a roller mechanism (not shown) movable along the second guide rail 32.

The post frame 50 is fixed to the lower side of the moving carriage 40. The post frame 50 includes a plurality of posts connected to each other to form a telescopic structure. Consequently, the length of the post frame 50 may increase or decrease in the vertical direction of the inspection room in a state in which the post frame 50 is fixed to the moving carriage 40.

The X-ray irradiator 10 generates and radiates X-rays toward the subject. The X-ray irradiator 10 includes an X-ray tube 11 to generate X-rays and a collimator 72 to guide the generated X-rays toward the subject.

The high voltage generator 20 generates high voltage to generate X-rays. The high voltage generator 20 is connected to the X-ray irradiator 10 so that high voltage generated by the high voltage generator 20 is supplied to the X-ray irradiator 10. When high voltage is supplied to the X-ray irradiator 10, X-rays are generated by collision between thermal electrons in the X-ray tube 11. The generated X-rays are radiated toward the subject via the collimator 12.

A rotary joint 60 is disposed between the X-ray irradiator 10 and the post frame 50. The rotary joint 60 couples the X-ray irradiator 10 to the post frame 50 and supports load applied to the X-ray irradiator 10. The rotary joint 60 includes a first rotary joint 62 connected to the lower end of the post frame 50 and a second rotary joint 61 connected to the X-ray irradiator 10.

The second rotary joint 61 is disposed so as to be rotatable on a plane perpendicular to the ceiling of the inspection room. The first rotary joint 62 is disposed so as to be rotatable about the central axis of the post frame 50 extending in the vertical direction of the inspection room.

The drive device 70 provides drive force to shift/move the position of the X-ray irradiator 10 within the inspection room. The drive device 70 may be an electric motor. The drive device 70 may include a plurality of drive devices connected to the second guide rail 32, the post frame 50 and the rotary joint 60.

The drive devices 70 may be disposed at various positions in consideration of design convenience. For example, a drive device to move the second guide rail 32 may be disposed near the first guide rail 31, a drive device to shift the moving carriage 40 may be disposed near the second guide rail 32, and a drive device to increase or decrease the length of the post frame 50 may be disposed in the moving carriage 40. Also, a drive device to rotate the X-ray irradiator 10 may be disposed near the rotary joint 60.

The drive device 70 may be connected to a power transmission unit (not shown), by which the drive devices 70 linearly move or rotate the X-ray irradiator 10 so as to controllably change the position of the X-ray irradiator 10 within the inspection room or the direction in which the X-ray irradiator 10 radiates X-rays. The power transmission unit (not shown) may include a belt and pulley, a chain and sprocket, and a shaft, which are generally well known to be used to provide power transmission of this type.

The X-ray irradiator 10 may be provided with a shift grip 80 configured to be held by an inspector/operator of the radiographic apparatus 1. The shift grip 80 is fixed to the X-ray irradiator 10. The inspector may apply force or torque to the shift grip 80 while holding the shift grip 80 to manually shift the X-ray irradiator 10.

The controller 3 is connected to the components of the capturing device 2 to control the components of the capturing device 2. The controller 3 may include a computer connected to the components of the capturing device 2 through a wired interface.

For example, the controller 3 may be connected to the drive device 70 to control the drive device to shift the X-ray irradiator 10 to a desired position. Also, the controller 3 may be connected to the high voltage generator 20 to control the high voltage generator 20 to generate high voltage to generate X-rays.

The inspector may input set values for the components of the capturing device 2 and then manipulate the components of the capturing device 2. Accordingly, the radiographic apparatus 1 includes a manipulation device to allow the inspector to input commands to control the capturing device 2. The manipulation device is connected to the controller 3.

The manipulation device is mounted to one of the components of the capturing device 2. Generally, the manipulation device is mounted to the X-ray irradiator 10 in consideration of a pattern of movement of the inspector while in the inspection room.

However, if the manipulation device is fixedly mounted to the X-ray irradiator 10, the position of the manipulation device would be changed when the position of the X-ray irradiator 10 is changed. As a result, the manipulation device may be beyond the inspector's reach or may be located where manipulation of the manipulation device by the inspector is difficult.

For this reason, in accordance with one aspect of the invention, the radiographic apparatus 1 includes a detachable manipulation device which is connected to the controller 3 in a wireless fashion using a wireless interface while in a state in which the manipulation device is separated from the capturing device 2.

Figure 2A:
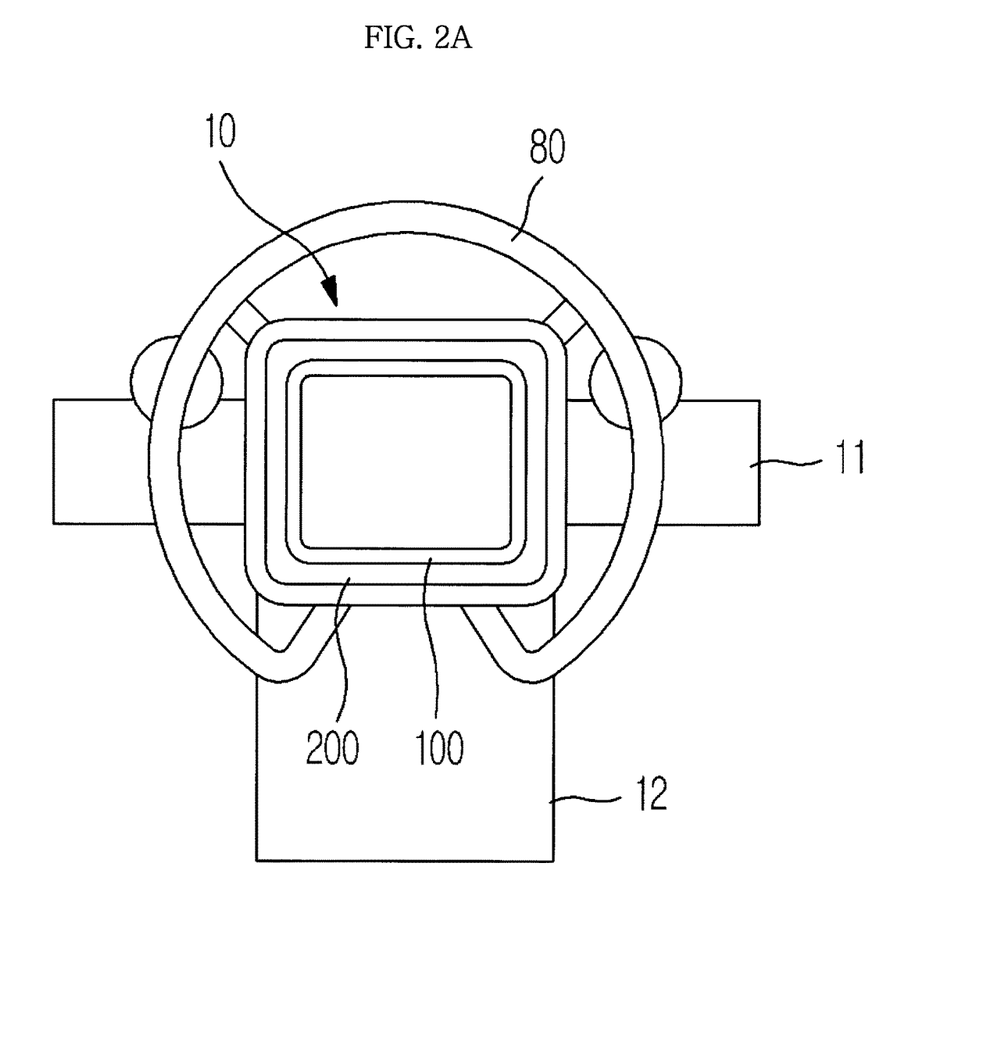
FIG. 2A and FIG. 2B are views illustrating a detachable manipulation device of the radiographic apparatus according to the embodiment of the present invention.
Figure 2B:
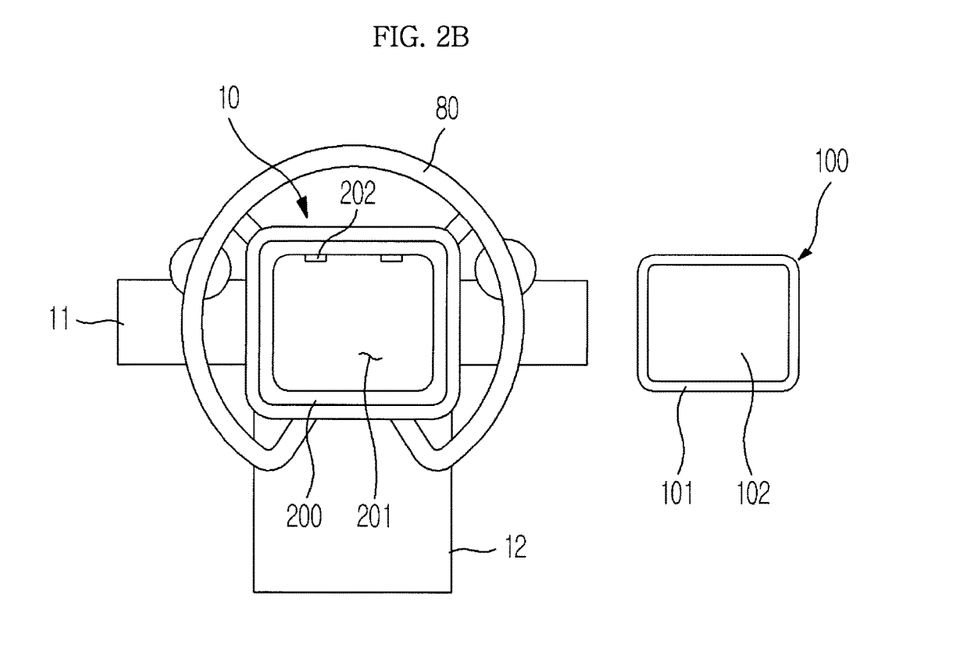

FIGS. 2A and 2B are views showing a detachable manipulation device 100 of the radiographic apparatus according to an embodiment of the present invention.

As shown in FIGS. 2A and 2B, the manipulation device 100 includes a case 101 open at one side thereof and a manipulation panel 102 disposed at the open side of the case 101.

The manipulation panel 102 may include a display panel to display states of the components of the capturing device 2 and a touch panel to allow the inspector to input commands by touch. Manipulation may be input using various manners in addition to touch. For example, a button may be used to input commands. Also, the manipulation device 100 may include a mobile device, such as a tablet PC.

A docking device 200 is disposed at one side of the X-ray irradiator 10. The manipulation device 100 is fixedly mounted to the docking device 200. The docking device 200 is connected to the controller 3 shown in FIG. 1. The docking device 200 includes a mount hole 201 formed in a shape corresponding to the manipulation device 100 and fixing protrusions 202 to fix the manipulation device 100.

In a state in which the manipulation device 100 is mounted to the docking device 200, power from the docking device 200 is supplied to the manipulation device 100. In this case, the manipulation device 100 is connected to the docking device 200 through a wired interface.

In a state in which the manipulation device 100 is separated from the docking device 200, power from a battery provided in the manipulation device 100 is supplied to the manipulation device 100. In this case, the manipulation device 100 is connected to the docking device 200 through a wireless interface. Consequently, it may be possible for the inspector to manipulate the components of the capturing device 2 irrespective of where the X-ray irradiator 10 is located.

Details of the manipulation device 100 and the docking device 200 are described next.

Figure 3:
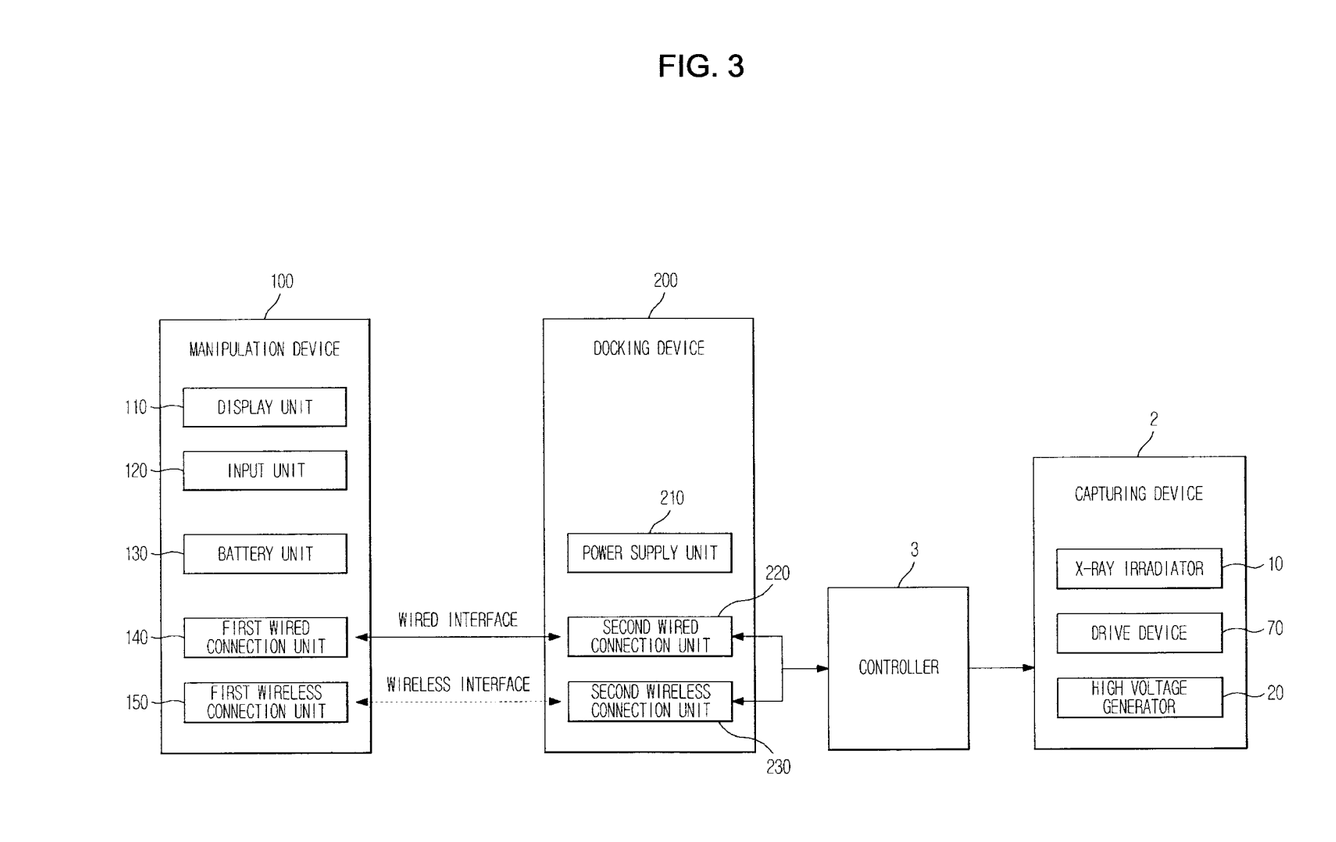
FIG. 3 is a view illustrating the construction of a manipulation device and a docking device of the radiographic apparatus according to the embodiment of the present invention.
Figure 4:
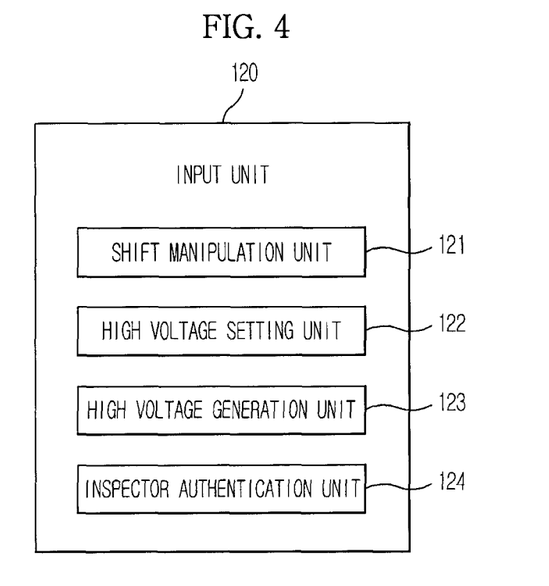
FIG. 4 is a view illustrating the construction of an input unit of the manipulation device of the radiographic apparatus according to the embodiment of the present invention.

FIG. 3 is a view illustrating the construction of the manipulation device and the docking device of the radiographic apparatus 1 according to an embodiment of the present invention, and FIG. 4 is a view illustrating the construction of an input unit of the manipulation device of the radiographic apparatus 1 according to an embodiment of the present invention.

As shown in FIG. 3, the manipulation device 100 includes a display unit 110 to display states of the components of the capturing device 2, an input unit 120 to allow the inspector to input commands, a battery unit 130 to supply power to the manipulation device 100 in a state in which the manipulation device 100 is separated from the docking device 200, and a first wired connection unit 140 and first wireless connection unit 150 connected to the docking device 200. The docking device 200 includes a power supply unit 210 to supply power to the manipulation device 100 and to charge the battery unit 130 of the manipulation device 100, and a second wired connection unit 220 and second wireless connection unit 230 connected to the manipulation device 100.

The display unit 110 displays states of set values of the components of the capturing device 2. The display unit 100 may include a display panel.

The input unit 120 allows the inspector to input commands to control the components of the capturing device 2. The input unit 120 may include a touch panel or buttons, as previously noted. The details of the input unit 120 will be described later.

When the manipulation device 100 is mounted to the docking device 200, the first wired connection unit 140 is connected to the second wired connection unit 220 of the docking device 200. When the first wired connection unit 140 is connected to the second wired connection unit 220, an electric signal to control the capturing device 2 is transmitted and received between the manipulation device 100 and the docking device 200 using a wired interface. The wired interface may include serial communication, such as RS232, RS422 and RS485, USB, IEEE1394 and LAN. However, the wired interface may also include various wired communication modes using wired communication modules.

When the manipulation device 100 is mounted to the docking device 200, the battery unit 100 of the manipulation device 100 is connected to the power supply unit 210 of the docking device 200. The battery unit 130 is charged with power supplied from the power supply unit 210. The battery unit 130 is charged using general charging methods.

The first wired connection unit 140 of the manipulation device 100 and the second wired connection unit 220 of the docking device 200 may include connectors through which the first wired connection unit 140 and the second wired connection unit 220 are connected to each other. Also, the battery unit 130 of the manipulation device 100 and the power supply unit 210 of the docking device 200 may include connectors through which the first wired connection unit 140 and the second wired connection unit 220 are connected to each other. The first wired connection unit 140 and the battery unit 130 of the manipulation device 100 may not include individual connectors but a single connector. In the same manner, the second wired connection unit 220 and the power supply unit 210 of the docking device 200 may not include individual connectors but a single connector.

When the manipulation device 100 is separated from the docking device 200, power from the battery unit 130 is supplied to the manipulation device 100. At this time, the first wireless connection unit 150 of the manipulation device 100 is connected to the second wireless connection unit 230 of the docking device 200 using a wireless interface. When the first wireless connection unit 150 is connected to the second wireless connection unit 230, an electric signal to control the capturing device 2 is transmitted and received between the manipulation device 100 and the docking device 200 using the wireless interface. The wireless interface may include infrared (IR) communication, radio frequency (RF) communication, Bluetooth communication, Wi-Fi communication and wireless USB communication. However, the wireless interface may also include various wireless communication modes using wireless communication modules.

In the above description, the second wireless connection unit 230 is provided at the docking device 200. However, the second wireless connection unit 230 may be provided as a separate device or as a part of the controller 3.

As shown in FIG. 4, the input unit 120 includes a shift manipulation unit 121 to input a position for the X-ray irradiator 10 and direction for the radiation of its X-rays, a high voltage setting unit 122 to set a value of high voltage to generate the X-rays, a high voltage generation unit 123 to input commands to generate the high voltage, and an inspector authentication unit 124 to authenticate an inspector/operator of the radiographic unit 1.

The shift manipulation unit 121 allows the inspector to input commands to control the drive device 70 to shift the X-ray irradiator 10 to a desired set position to at which X-rays are to be generated and to a desired set direction in which the X-rays are to be radiated from the X-ray irradiator 10 towards the subject. The inspector may manually input shift direction (via rotation control of pivot unit 60) and shift position (via distance control of guide rail 30, carriage 40 and post frame 50) by control of the drive device 70 through the shift manipulation unit 121. Alternatively, the inspector may set frequently used X-ray radiation positions and directions in a macro form through the shift manipulation unit 121 and may shift the X-ray irradiator 10 to a predetermined position and direction through one input.

The high voltage setting unit 122 allows the inspector to set a value of high voltage of the high voltage generator 20. The high voltage generation unit 123 allows the inspector to input commands to control the high voltage generator 20 to supply high voltage to the X-ray irradiator 10.

Since the manipulation device 100 is connected to the docking device 200 using the wireless interface, a particular advantage of the present invention is that it allows the inspector to control the high voltage generator 20 from outside the inspection room so that the inspector is not exposed to radiation, yet, while the inspector is inside the room, has direct access (that is, close contact) with the patient and the radiographic apparatus 1 so as to ensure that the position of the X-ray irradiator 10 is accurately set.

The inspector authentication unit 124 allows the inspector/operator of the radiographic apparatus 1 to input his/her identification and password. When the inspector wishes to mount or separate the manipulation device 100 to or from the docking device 200 during the radiographic operation, the inspector may input his/her identification and password through the inspector authentication unit 124, thereby preventing the radiographic operation from being performed by an unauthorized person.

Thus, with the present invention, duplicate controls for setting and initiating a radiographic operation are not required, thereby preventing someone else from manipulating a duplicate control and causing premature operation of the radiographic apparatus 1.

Figure 5:
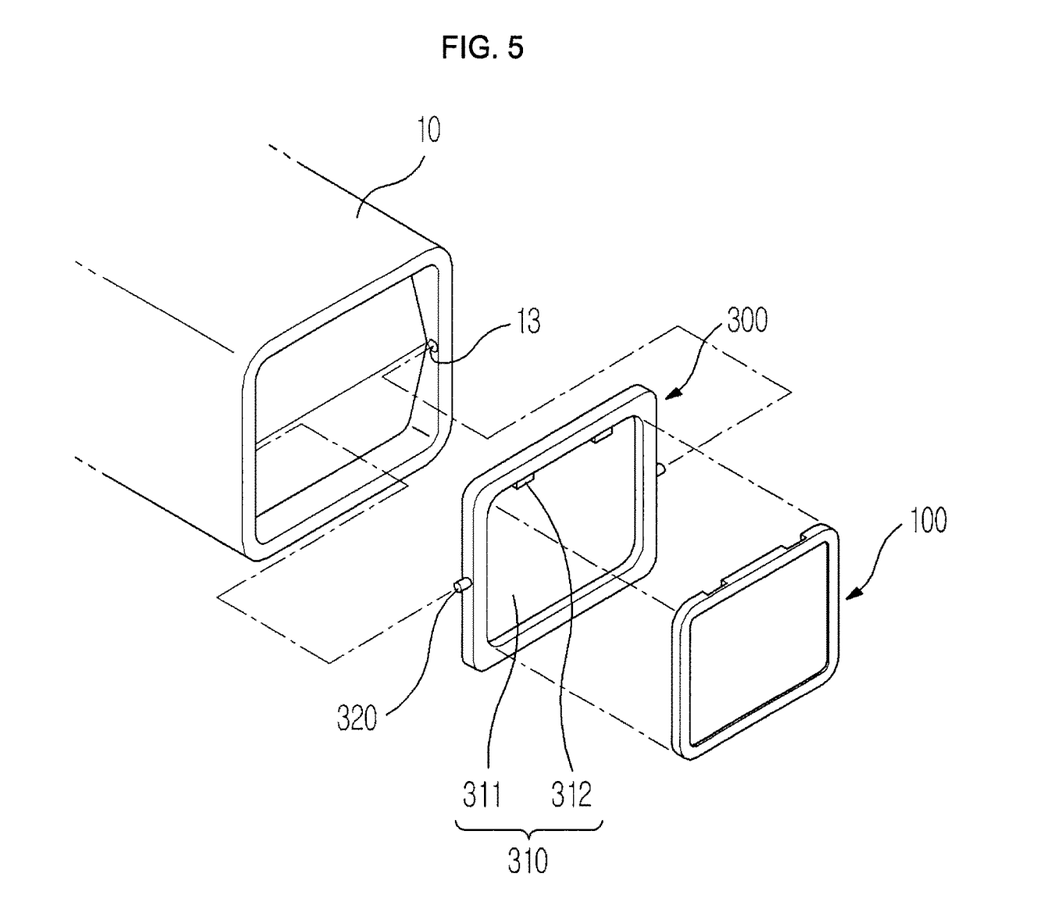
FIG. 5 and FIG. 6 are views illustrating a manipulation device and a docking device of a radiographic apparatus according to another embodiment of the present invention.
Figure 6:
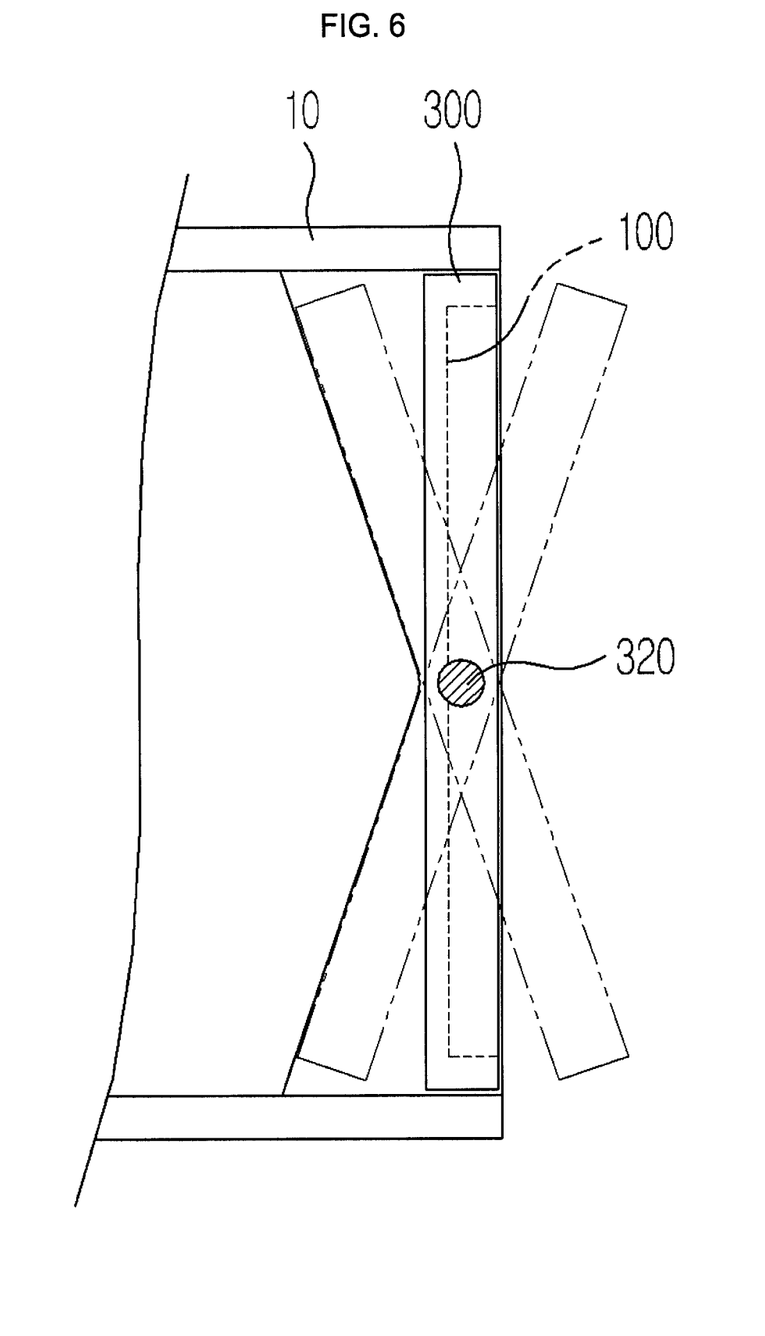

FIGS. 5 and 6 are views showing a manipulation device 100 and a docking device 300 of a radiographic apparatus according to another embodiment of the present invention.

As shown in FIGS. 5 and 6, the docking device 300 includes a mounting unit 310 to which the manipulation device 100 is mounted and a rotary unit 320 rotatably coupled to an X-ray irradiator 10.

The rotary unit 320 includes rotary protrusions coupled to rotary grooves 13 provided at the X-ray irradiator 10. The rotary protrusions may be electrically connected to the rotary grooves 13.

The mounting unit 310 includes a mount hole 311 formed in a shape corresponding to the manipulation device 100 so that the manipulation device 100 can be mounted in the mount hole 311 and fixing protrusions 312 to fix the manipulation device 100 to mounting unit 310. When the manipulation device 100 is mounted in the mount hole 311, the manipulation device 100 is electrically connected to the docking device 300.

When the manipulation device 100 is mounted to the docking device 300, the manipulation device 100 is rotatable along with the docking device 300. Consequently, it may be possible for the inspector to rotate the manipulation device 100 to a position at which easy input is performed.

As is apparent from the above description, the manipulation device may be detachably mounted to the capturing device and may be connected to the components of the capturing device in a wireless fashion. Consequently, it may be possible for the inspector to manipulate the component of the capturing device irrespective of where the capturing device is located and to also prevent a radiographic operation from being performed by an unauthorized person.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A ceiling mounted X-ray device that generates radiographic images, the device comprising:
    a capturing device to generate X-rays and to radiate the X-rays toward a subject to capture an image of the subject, the capturing device including an X-ray irradiator to generate and radiate the X-rays towards the subject;
    a pair of guide rails arranged at a predetermined angle in which a first guide rail is slidable and a second guide rail is configured to be mounted to a ceiling;
    a carriage having the capturing device disposed thereon and being moveable along the second guide rail;
    a first drive device arranged to move the first slidable guide rail of the pair of guide rails;
    a second drive device arranged to rotate the X-ray irradiator about an axis orthogonal to the ceiling and proceeding through the carriage;
    a controller communicatively coupled to the ceiling x-ray device to control an X-ray position and an X-ray irradiation direction of the capturing device;
    a manipulation device detachably mounted to the capturing device to allow an input of commands to control the capturing device; and
    a wireless interface to control the capturing device when the manipulation device is detached from the capturing device,
    wherein the manipulation device includes a first wired connection unit, a first wireless connection unit and a battery unit.

2. The ceiling mounted X-ray device according to claim 1, wherein the wireless interface comprises any one selected from among infrared (IR) communication, radio frequency (RF) communication, Bluetooth communication, Wi-Fi communication and wireless USB communication.

3. The ceiling mounted X-ray device according to claim 1, wherein the first drive device is arranged to linearly move the X-ray irradiator, and the manipulation device is detachably mounted to the X-ray irradiator.

4. The ceiling mounted X-ray device according to claim 1, wherein
    the capturing device comprises a high voltage generator to generate high voltage to generate the X-rays, and
    the manipulation device manipulates a set value of the high voltage generator when the manipulation device is detached from the capturing device.

5. The ceiling mounted X-ray device according to claim 1, wherein
    the capturing device comprises a high voltage generator to generate high voltage to generate the X-rays, and
    the manipulation device manipulates the high voltage generator to generate high voltage when the manipulation device is detached from the capturing device.

6. The ceiling mounted X-ray device according to claim 1, wherein
    the capturing device includes a shifter to shift an irradiation position and direction of the X-rays, and
    the manipulation device manipulates the shifter when the manipulation device is detached from the capturing device.

7. The ceiling mounted X-ray device according to claim 1, wherein the manipulation device includes an inspector authentication to authenticate an operator.

8. A ceiling mounted X-ray device that generates radiographic images, comprising:
    a capturing device to generate X-rays and to radiate the X-rays towards a subject to capture an image of the subject, the capturing device including an X-ray irradiator to generate and radiate the X-rays towards the subject;
    a pair of guide rails arranged at a predetermined angle in which a first guide rail is slidable and a second guide rail is configured to be mounted to a ceiling;
    a carriage having the capturing device disposed thereon and being moveable along the second guide rail;
    a first drive device arranged to move the first slidable guide rail of the pair of guide rails;
    a second drive device arranged to rotate the X-ray irradiator about an axis orthogonal to the ceiling and proceeding through the carriage;
    a post frame that is fixed to the lower side of the carriage and telescopically extends toward a subject;
    a controller communicatively coupled to the capturing device to control an X-ray position and an X-ray irradiation direction of the capturing device;
    a manipulation device connected to the controller to allow an input of commands to control the capturing device and to display information on the capturing device; and
    a docking device communicatively coupled to the controller and wherein the manipulation device is detachably mounted to the docking device to control the capturing device,
    wherein the manipulation device includes a first wired connection unit, a first wireless connection unit and a battery unit, and
    the docking device includes a second wired connection unit connected to the first wired connection unit, a second wireless connection unit wirelessly connectable to the first wireless connection unit when the manipulation device is separated from the docking device, and a power supply unit.

9. The ceiling mounted X-ray device according to claim 8, wherein the manipulation device comprises a wireless connection unit to transmit to and receive a wireless signal from the controller.

10. The ceiling mounted X-ray device according to claim 9, wherein the wireless connection unit comprises any one selected from among an IR module, RF module, Bluetooth module, Wi-Fi module and wireless USB module.

11. The ceiling mounted X-ray device according to claim 10, wherein the power supply unit supplies power to the manipulation device when the manipulation device is mounted to the docking device.

12. The ceiling mounted X-ray device according to claim 11, wherein the wired connection unit comprises any one selected from among a serial communication module, USB module, IEEE1394 module and LAN module.

13. The ceiling mounted X-ray device according to claim 11, wherein the power supply unit and the second wired connection unit are integrated.

14. The ceiling mounted X-ray device according to claim 8, wherein the manipulation device includes a display unit to display information and an input unit to input commands.

15. The ceiling mounted X-ray device according to claim 14, wherein the input unit comprises a touch panel configured to respond to tactile input.

16. The ceiling mounted X-ray device according to claim 14, wherein the input unit comprises a shift manipulation unit to manipulate a position at which the X-rays are generated and a direction in which the X-rays are radiated.

17. The ceiling mounted X-ray device according to claim 14, wherein the input unit comprises a high voltage setting unit to set a value of high voltage to generate the X-rays.

18. The ceiling mounted X-ray device according to claim 14, wherein the input unit comprises a high voltage generation unit to generate the X-rays.

19. The ceiling mounted X-ray device according to claim 14, wherein the input unit comprises an inspector authentication unit to authenticate an operator.

20. The ceiling mounted X-ray device according to claim 8, wherein the battery unit supplies power to the manipulation device when the manipulation device is detached from the capturing device.

21. The ceiling mounted X-ray device according to claim 8, wherein the first drive device is arranged to linearly move the capturing device.

22. The ceiling mounted X-ray device according to claim 8, wherein the docking device includes a mount hole for receiving the manipulation device and fixing protrusions to fix the manipulation device.

\* \* \* \* \*